United States Patent [19]

Fedorov et al.

[11] Patent Number: 4,515,157
[45] Date of Patent: May 7, 1985

[54] CORNEAL INCISION MARKER

[75] Inventors: Svyatoslav N. Fedorov; Evgeny I. Degtev; Vladimir N. Golubev; Sergei V. Khromov; Igor A. Yatsenko; Alexandr A. Karavaev, all of Moscow, U.S.S.R.

[73] Assignee: Moskovsky Nauchno-Issledovatelsky Institut Mikrokhirurgii Glaza, Moscow, U.S.S.R.

[21] Appl. No.: 458,789

[22] Filed: Jan. 18, 1983

[30] Foreign Application Priority Data

Jul. 28, 1982 [SU] U.S.S.R. .............................. 3464601

[51] Int. Cl.³ .............................................. A61F 9/00
[52] U.S. Cl. ................. 128/303 R; 128/305; 128/316; 33/191
[58] Field of Search ............... 128/316, 305, 303 R, 128/339; 33/189, 191, 1 SP, 178 D, 199 R; 30/360, 366

[56] References Cited

U.S. PATENT DOCUMENTS

| | | | |
|---|---|---|---|
| 1,044,299 | 11/1911 | Trundle | 33/191 |
| 2,519,908 | 8/1950 | Howard et al. | 33/191 |
| 2,860,421 | 11/1958 | Smith | 33/191 |
| 3,318,010 | 5/1967 | Mahl | 33/191 |
| 3,502,070 | 3/1970 | Bliss | 128/303 R |
| 4,069,586 | 1/1978 | Skelton | 30/360 |
| 4,319,575 | 4/1982 | Bonte | 128/305 |
| 4,336,805 | 6/1982 | Smirmaul | 128/305 |
| 4,357,941 | 11/1982 | Golubkov et al. | 128/316 |
| 4,406,285 | 9/1983 | Villasenor et al. | 128/303 R |
| 4,417,579 | 11/1983 | Soloviev et al. | 128/303 R |

Primary Examiner—C. Fred Rosenbaum
Assistant Examiner—Gene B. Kartchner
Attorney, Agent, or Firm—Fleit, Jacobson, Cohn & Price

[57] ABSTRACT

The invention relates to ophthalmology and, more particularly, to a corneal incision marker adapted for use in surgical treatment, notably that of myopia.

An instrument of this invention comprises a case in the form of a bush accommodating a sight, and plates in planar arrangement at right angles to the plane of the sight. The plates are brought into contact with the cornea leaving indentations which serve as guidelines to perform incisions. According to the invention, each plate is mounted on a separate holder, the latter being attached movably radially with respect to the bush, the holders being rigidly secured in their entirety to said bush, and provision is made for a drive to effect smooth synchronized movement of the plate holders.

4 Claims, 2 Drawing Figures

CORNEAL INCISION MARKER

The invention herein disclosed relates to opthalmology and, more particularly, to a corneal incision marker suitable for use in surgical removal of myopia, astigmatism and compound myopic astigmatism.

Over the recent years much interest was generated in a novel surgical procedure employed in the treatment of such conditions as myopia, astigmatism and compound myopic astigmatism. In performing such an operation, the ophthalmologist makes a series of external partial thickness incisions of the corneal periphery. Arrangement of the incisions varies depending upon the condition to be treated and state of the patient's eye. Initially, the incisions were made free-hand with the choice of their arrangement and placement reserved to the surgeon.

It stands to reason that the resultant incisions are subject to considerable variation affecting their position both relative to each other and to the optical center and central optical zone of the cornea.

However, even the slightest variation in making incisions may lead to undesirable results for the patient, namely, altering the pathway of the light rays passing through the eye and consequently resulting in distorted perception of the image.

Patent application Ser. No. 373,492 now U.S. Pat. No. 4,417,579 teaches a corneal incision marker adapted for marking out the corneal surface depending on the type of ocular disease which ensured obtainment of highly accurate incisions and, therefore, reliable surgical effect.

The above-mentioned marker comprises a case in the form of a bush which is centrally perforated to accommodate a sighted centering means, and plates disposed at one end thereof in planar arrangement at right angles to the plane of the sighted means, adapted to be brought into contact with the cornea to be marked out, the plates being provided with curvilinear edges having a thickness sufficient to cause elastic deformation of the cornea without rupturing on exerting a pre-set pressure, mutual arrangement of the plates being variably conditionable to suit the desired placement of incisions during surgery.

Such a device, while considerably reducing the complexity of surgical protocol and increasing the operative accuracy is of utility limited to a given size of the central optical zone which changes with the patient.

Therefore, the surgeon requires a set of such markers fabricated to a high degree of precision which significantly increases the cost of instrumentation.

Furthermore, such markers cover only a discrete range of central optical zone sizes, hence, in some instances the marking out is subject to approximation which adversely affects the operative accuracy.

It is an object of this invention to provide a corneal incision marker which can be adjusted to the individual diameter of the central optical zone.

Another object of this invention lies in providing a marking out procedure of greater accuracy and shorter duration and, therefore, reducing the time of surgery.

It is still another object of this invention to provide a device reducing the workload on the surgeon.

The aforesaid objects and their corollaries are accomplished by the provision of a corneal incision marker which comprises a case in the form of a bush which is centrally perforated to accommodate a sighted centering means, and plates in planar arrangement at right angles to the plane of said sighted means, adapted to be brought into contact with the cornea to be marked out and provided with curvilinear marking edges, mutual arrangement of the plates being variably conditionable to suit the desired placement of incisions during surgery, according to the invention, each plate is mounted on a separate holder for movement radially with respect to the bush, the holders being rigidly secured in their entirety to said bush, and provision is made for a drive to effect smooth synchronized movement of the holders with the plates.

An advantage of this invention resides in that the plate attachment can be adjusted to the desired central optical zone.

According to one embodiment of the invention, a corneal incision marker comprises a holder with a tapering portion having its tapered tip facing the bush, and a drive which is essentially a coupling nut in threaded movable engagement with the bush whereby smooth spatial adjustment of the radially disposed plates is achieved.

In another embodiment of the invention, a corneal incision marker comprises a coupling nut provided with a flange facing the plate holders and engaging the tapering portions thereof whereby adjustment of the central optical zone diameter is made continuous.

In still another embodiment of the invention, a corneal incision marker is provided with a scale placed on the lower edge of the coupling nut, and one of the holders is provided with a mark.

The latter embodiment is advantageous in that it permits visual setting of the central optical zone diameter to be effected with high accuracy without any additional measurements.

The invention will be now described, by way of example only, with reference to the accompanying drawings, wherein.

Figure 1:
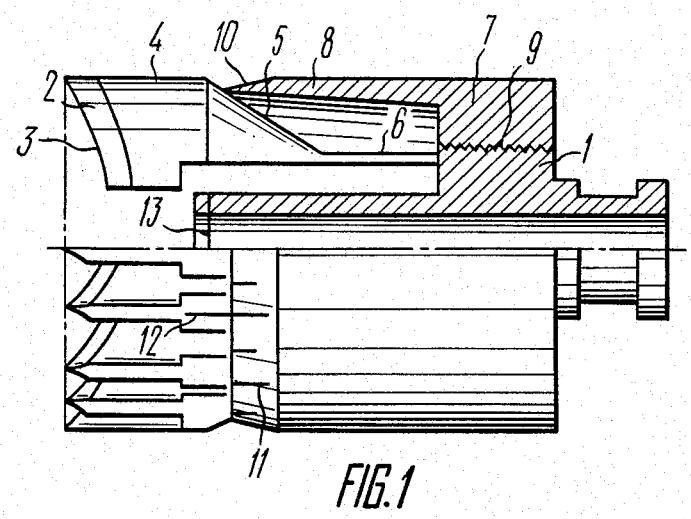
FIG. 1 is a sectional partially cut away view of the corneal incision marker according to the invention.

Referring now to FIG. 1, there is shown a corneal incision marker, which comprises a case I and a plurality of arcuate plates 2. All plates 2 are fabricated from a material highly convenient for sterilization, for example, stainless alloy or an alloy with a rust-proof coating. A marking edge 3 of the plates 2 is made sharp and curved with a radius of curvature to match that of the patient's corneal surface. The thickness of the edges 3 is chosen to provide for elastic deformation of the cornea without rupturing the same and commonly falls in the range of from 0.1 to 0.2 mm.

Each plate 2 is mounted on a separate holder 4 which is a part of a certain configuration provided with a tapering portion 5 formed integrally with a cylindrical portion 6, being rigidly secured to the case I allowing for a degree of elasticity. The plates 2 are secured adjacent the greater base end of the tapering portion 5.

It will thus be seen that each holder 4 conjointly with the plate 2 mounted thereon is capable of radial movement causing change in the central optical zone diameter. It will be obvious to those skilled in the art that such a displacement can be produced by a variety of means.

However, in the preferred embodiment use is made of a coupling nut 7 with a flange 8 facing in the direction of the tapering portion 5. Movement of this nut 7 along the outer portion of the case I is made possible by means of a special thread 9. The flange 8 is provided with a sharpened portion 10 and a graduated scale 11 marked thereon. One of the holders is provided with a mark 12.

Figure 2:
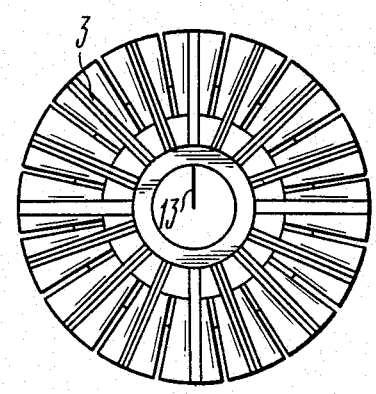
FIG. 2 is a view on line A of FIG. 1.

FIG. 2 shows a sighted centering means 13 disposed within the centrally perforated case 1.

In using the device disclosed hereinabove the surgeon performs the following steps.

The surgeon moves the coupling nut 7 back until the sharpened portion 10 of the flange 8 is disengaged from tapering portion 5. At this position the internal diameter formed by the plates 2 corresponds to the maximum possible diameter of the central optical zone.

Further rotation of the coupling nut 7 results in the sharpened portion 10 of the flange 8 engaging the cylindrical portion 6 of the separate holders 4. At the same time the plates 2 undergo smooth radial displacement with simultaneous change in diameter of the central optical zone.

The desired central optical zone diameter is set using the dial 11 and mark 12.

Grasping the marker with a forceps by the case I the surgeon brings the tip of the sights 13 against the corneal optical center, whereupon the marking plates 2 are pressed against the corneal surface, which is stained with brilliant green prior to the procedure, for 2-3 sec. On removing the device the well-observed corneal indentations persist and can be used by the surgeon as guidelines for making partial thickness incisions.

The use of this invention will sharply reduce the time of marking out the cornea and, as a consequence, the entire length of surgery, as well as improve the marking out accuracy by 2.5 to 3 times.

Moreover, by ruling out displacement of the corneal optical center during the marking out, the hazard of developing post-operative astigmatism is avoided. The use of this invention also alleviates the workload experienced by the surgeon.

It is understood that the embodiments of the invention, herewith shown and described, are to be perceived as preferred examples of the same by those skilled in the art, and that various changes and improvements may be resorted to, without departing from the spirit of the invention and the scope of the subjoined claims.

We claim:

1. A device for marking locations for incisions on the cornea of an eye, said device comprising: an elongated, hollow case defining a bush; sight means for centering said device over the cornea, said sight means being positioned within said hollow case; multiple, radially oriented plates having sharpened, curvilinear edges for marking said incision locations on the cornea; means for holding said plates, said holding means having an outer surface and including a tapered surface which tapers inwardly from said outer surface in the direction of said case and away from said curvilinear edges, said holding means having a cylindrical end which is rigidly secured to said case, said plates being mounted on the holding means on an end opposite said tapered surface and extending outwardly of said bush; and drive means movably coupled to said case for engaging said tapered surface of said holding means for providing smooth synchronized movement to radially adjust the positions of said holding means and said plates.

2. A marker as claimed in claim 1, wherein the tapered surface of the holding means faces the bush, and said drive means includes a coupling nut in movably threaded engagement with the bush.

3. A marker as claimed in claim 2, wherein said coupling nut includes a flange facing in the direction of the plate holding means and engaging the tapering portion thereof.

4. A marker as claimed in claim 3, wherein said flange of said coupling nut includes a peripheral surface that has a graduated scale thereon and the holding means includes a mark adjacent said graduated scale to set the desired radial positions of said plates.

* * * * *